(12) United States Patent
Courtney et al.

(10) Patent No.: US 7,521,696 B2
(45) Date of Patent: Apr. 21, 2009

(54) METHOD AND APPARATUS FOR ANALYZING A DYNAMIC SAMPLE

(75) Inventors: Patrick Courtney, Ealing (GB); Robert Hoult, Beaconsfield (GB); Alistair Fitch, Maidenhead (GB); Steve Bush, Hibil Wycombe (GB); Shab Ladha, Chalfont St Gales (GB); Colin Blackmore, Welwyn Garden City (GB)

(73) Assignee: PerkinElmer Singapore PTE Ltd., Singapore (SG)

( * ) Notice: Subject to any disclaimer, the term of this patent is extended or adjusted under 35 U.S.C. 154(b) by 42 days.

(21) Appl. No.: 11/718,788

(22) PCT Filed: Dec. 21, 2005

(86) PCT No.: PCT/GB2005/004954

§ 371 (c)(1),
(2), (4) Date: Nov. 16, 2007

(87) PCT Pub. No.: WO2006/067426

PCT Pub. Date: Jun. 29, 2006

(65) Prior Publication Data

US 2008/0217557 A1    Sep. 11, 2008

(30) Foreign Application Priority Data

Dec. 22, 2004  (GB)  ................................. 0428044.2
Aug. 2, 2005   (GB)  ................................. 0515845.6

(51) Int. Cl.
*G01N 21/64*  (2006.01)

(52) U.S. Cl. .................................................. 250/459.1

(58) Field of Classification Search ............... 250/459.1
See application file for complete search history.

(56) References Cited

U.S. PATENT DOCUMENTS

| 5,215,883 | A * | 6/1993 | Chu .......................... 204/452 |
| 6,462,345 | B1 * | 10/2002 | Simon et al. .............. 250/458.1 |
| 2003/0092884 | A1 * | 5/2003 | Lukyanov et al. ........... 530/350 |
| 2006/0087727 | A1 * | 4/2006 | Brooker ...................... 359/368 |
| 2007/0212677 | A1 * | 9/2007 | MacDonald et al. ........... 435/4 |
| 2008/0285123 | A1 * | 11/2008 | Funk et al. ................... 359/388 |

* cited by examiner

*Primary Examiner*—David P Porta
*Assistant Examiner*—Marcus H Taningco
(74) *Attorney, Agent, or Firm*—Barnes & Thornburg LLP

(57) ABSTRACT

A method of analysing a sample of biological material including components (2a to 2d) tagged with respective fluorescent labels (4a to 4d), comprises the steps of identifying a specific labeled component (2d) to be monitored, and irradiating with an energy beam at least one region (8) of the sample which substantially surrounds said specific component. The energy beam modifies the optical properties of labels in the region (8) such that they are distinguishable from the label (4d) associated with said specific component (2d). This assists the tracking of a specific component of interest as it moves through a sample. Apparatus for carrying out the method is also described.

10 Claims, 3 Drawing Sheets

METHOD AND APPARATUS FOR ANALYZING A DYNAMIC SAMPLE

FIELD OF THE INVENTION

The present invention relates to a method and apparatus for analysing a sample of biological material which includes moving components.

BACKGROUND

A conventional approach to tracking moving components in a sample is to determine changes relative to the background in order to identify regions which may be mobile components of interest. In fluorescence microscopy, the components of interest may be tagged by fluorescent labels or probes, making the task of distinguishing them from the background relatively straightforward.

Fluorescent molecules employed as labels typically have a specific excitation spectrum, being more strongly excited at some wavelengths and less strongly excited at others. They also have a specific emission spectrum, emitting more intensely at some wavelengths, and less intensely at others. The excitation and emission spectra may range from the ultraviolet to the infrared.

A wide range of fluorescent probes have been developed from chemical molecules, such as Rhodamine and Fluoroscein. Further fluorescent probes have been developed from molecules found in luminescent organisms, for example the *Aequorea* Jellyfish which has provided the Green Fluorescent Protein (GFP), and various corals providing DsRed and HcRed. These have been termed AFPs (*Aequorea* Fluorescent Proteins) and are described for example in J. Zhang, et al, Nature Reviews: Molecular Cell Biol., Vol 3, December 2002, pp 906-918; Y. A. Labas, Proc. Natl. Acad. Sci., 2002, Vol 99, pp 4256-4261; and M. V. Matz, Bioassay, Vol 24, pp 953-959.

The fluorescent probes may be associated with specific molecules of interest (DNA, RNA, proteins, carbohydrates, antibodies, etc). Alternatively they may be made to be sensitive to certain characteristics (ionic concentration, pH, voltage potential, temperature, the presence of a specific enzyme, the presence of specific enzyme substrates, force), altering their fluorescent properties according to these characteristics. These labels may be introduced into cells by passing through the cell membrane or by injection. Alternatively they may be formed internally as part of the normal functioning of the cell, in the case of the genetically encoded probes such as the AFPs.

In a known apparatus for imaging samples including fluorescent labels, a fluorescence microscope (FIG. 1) is fitted with an excitation light source which is capable of exciting one or more fluorescent probes at specific wavebands. The microscope is also fitted with suitable optical filters so that the light emitted from the probes may be observed at other wavebands. Examining the spatial and temporal distribution of light emitted provides information on the structure and dynamics of the sample.

The use of multiple labels provides information on the coincident localisation of labeled components, revealing, for example, the organization of the cytoskeleton of a cell. The fluorescence microscope is often fitted with an image acquisition system, comprising a light sensitive detector (sensitive from the ultraviolet to the infrared) such as a CCD camera or a combination of a scanner and a photomultiplier tube, and recording means such as a video recorder or computer system with a memory device, so that dynamic behaviour of the sample may be captured and analysed offline.

The system may employ a focus drive mechanism for altering the position of the imaging focus plane, thus allowing volumetric (XYZ) and volumetric time series (XYZT) data to be acquired. By selecting suitable excitation and/or emission wavebands and/or selecting suitable optical filter sets, volumetric multi-wavelength (XYWZ) and volumetric multi-wavelength time series (XYWZT) data may be acquired.

The microscope may also be fitted with additional apparatus to control the temperature, gas content and flow, introduce liquids, etc.

In order to gain a deeper understanding of the dynamic processes in a sample such as a living cell, an additional activating light beam may be provided (in many cases based on the excitation light source). The activating light beam may be directed to portions of the sample containing labels in such a manner that the intense light from this beam bleaches the label and reduces its fluorescence. By observing the subsequent development of fluorescence in this region, and elsewhere in the sample, information can be obtained on mechanisms of interaction and exchange of various labeled components (for example, as described in AxelRod, Biophys. J., 1977, Vol 18, pp 129-131; and Phair et al, Nature, 2000, Vol 404, pp 604-609).

Methods and apparatus for analysis of samples including fluorescent labels are disclosed in the present applicant's copending United Kingdom Patent Application No. 0419325.6, the contents of which are incorporated herein as reference material.

Moving components may often be distinguishable by their size, shape or trajectory, for example. However, this can be problematic if the components concerned are very similar in shape and size, or vary considerably in shape and size over time, or have unpredictable trajectories.

Existing approaches to addressing this problem include locating candidate particles and estimating the matches between frames. Examples are described in J. L. Barron, Fleet, D. J., and Beauchemin, S. (1994) Performance of optical flow techniques, International Journal of Computer Vision, 12(1):43-77; Nagel, H.-H. 1977, Analysing Sequences of TV-Frames: System Design Considerations, In Proc. Intern. Joint Conference on Artificial Intelligence, Cambridge, Mass., 626; Nagel, H.-H. 2000, Image Sequence Evaluation: 30 Years and Still Going Strong, In Proc. 15th Intern. Conf. Pattern Recognition, A. Sanfeliu, J. J. Villanueva, M. Vanrell, R. Alqu'ezar, J.-O. Eklundh, and Y. Aloimonos (Eds.), Vol. 1, 149-158. Los Alamitos, Calif.: IEEE Computer Society; M. Isard and A. Blake, Condensation—conditional density propagation for visual tracking, International Journal of Computer Vision 29(1), pp. 5-28, 1998; D. Comaniciu, V. Ramesh, and P. Meer, Kernel-Based Object Tracking, IEEE PAMI, vol. 25, no. 5, May 2003; Raffel M., Willert C., Kompenhans J (1998) Particle Image Velocimetry. Springer, Berlin; Stanislas, M., Kompenhans, J., Westerweel, J., Particle Image Velocimetry—Progress towards Industrial Application, Kluwer Academic Publishers, 2000.

Separate bleach and imaging scanning techniques are described in UK Patent Specification No. 2369739, and "Beam Control in a Scanning Microscope", J. Engelhardt/Leica, 5 Jun. 2002.

SUMMARY OF THE INVENTION

The present invention provides a method of analysing a sample of biological material including components tagged with respective fluorescent labels, the method comprising the steps of identifying a specific labeled component to be monitored, and irradiating with an energy beam at least one region of the sample which substantially surrounds said specific component so as to modify the optical properties of labels in the region such that they are distinguishable from the label associated with said specific component. This serves to assist the tracking of said specific component.

In embodiments of the invention, the energy beam may irradiate two or more regions which in combination substantially surround said specific component.

The one or more regions may substantially surround said specific component in two or three dimensions. They may define a complete or substantially complete geometric shape, such as an annulus (in two dimensions) or a hollow sphere (in three dimensions) for example.

In a preferred embodiment, the one or more regions define an enclosed area or volume which is elongate. In particular, it may be elongate in the direction of travel of said specific component.

It may be preferable to carry out one or more further irradiation steps, for example, periodically, or if said specific component has moved since the preceding irradiation step and/or if other labeled components have entered the one or more regions irradiated by the preceding irradiation step. Further irradiation may therefore assist in ensuring that said specific component continues to be distinguishable from other adjacent labeled components in a dynamic sample.

Advantageously the imaging apparatus may be configured to monitor the one or more irradiated regions and trigger a further irradiation in response to detection of additional labeled components entering the one or more regions. In this way, irradiation may be controlled so as to only occur when necessary, minimising the amount of radiation incident on the sample.

The invention further provides apparatus for analysing a sample including components tagged with respective fluorescent labels, the apparatus including:

means for irradiating the sample with an energy beam;
a support for holding the sample; and
control means for moving the energy beam and the sample relative to each other to irradiate at least one region of the sample which substantially surrounds the location of a specific component so as to modify the optical properties of labels in the region such that they are distinguishable from the label associated with said specific component.

DETAILED DESCRIPTION OF THE INVENTION

Prior art and embodiments of the invention will now be described by way of example and with reference to the accompanying schematic drawings, wherein:

FIG. 2A shows four components 2a to 2d in a sample, each tagged with a respective fluorescent label, 4a to 4d. The direction of travel of each component is indicated by a respective arrow, 6a to 6d.

FIG. 2B shows the same view as 2A, after a period of time has elapsed. It can be seen that an observer following component 2d may risk confusing it with component 2a which passes close to it.

Figure 3A:
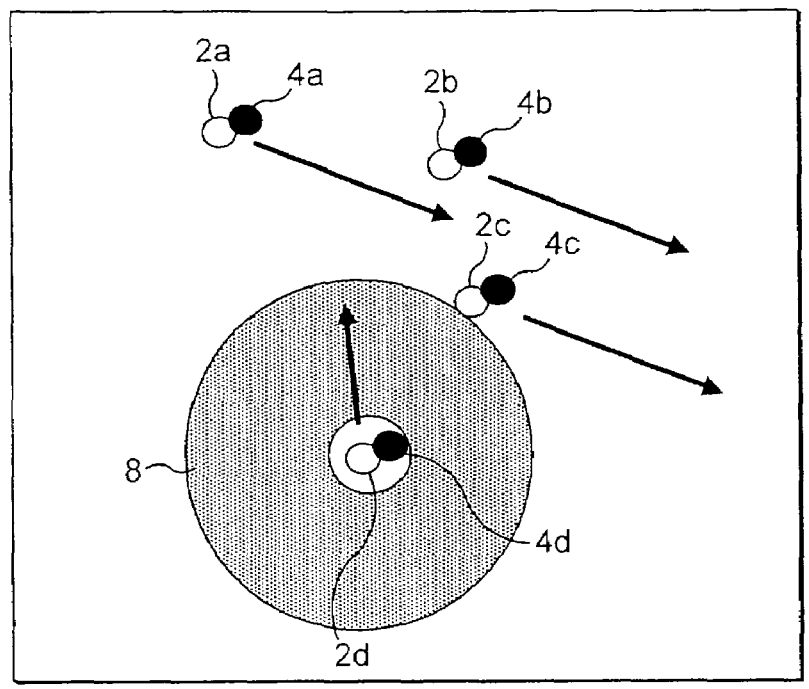
FIGS. 3A and 3B show images of part of a sample at two points in time and bleaching of a selected region according to an embodiment of the invention.

To address this issue, according to an embodiment of the invention, an annular region 8 surrounding the component of interest 2d is irradiated with an energy beam, as shown in FIG. 3A. For example, a light beam may be used, having an intensity in the annular region 8 sufficient to bleach any fluorescent label on which it is incident.

Figure 1:
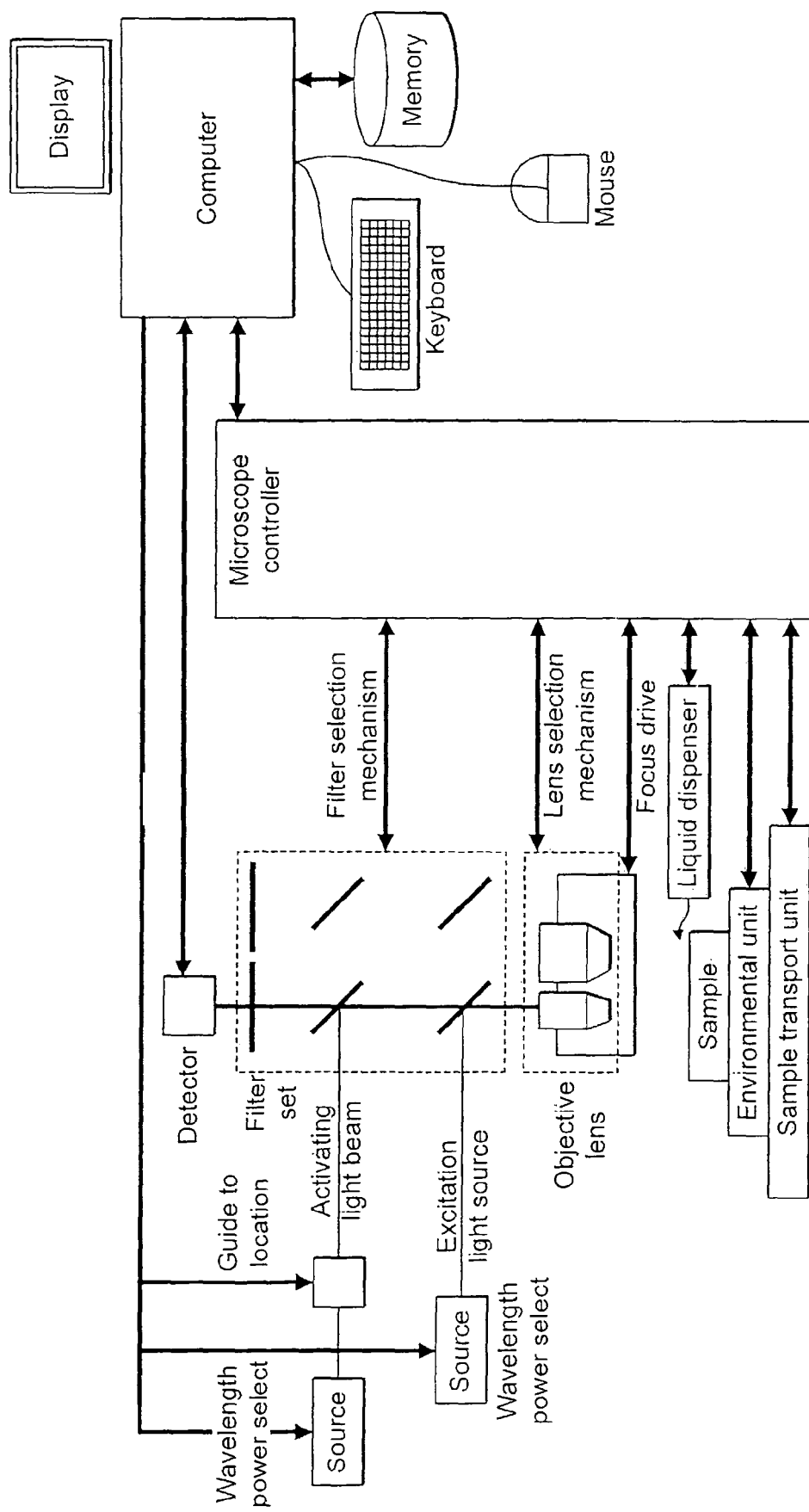
FIG. 1 shows a block diagram of a known apparatus for investigating biological samples.
Figure 2A:
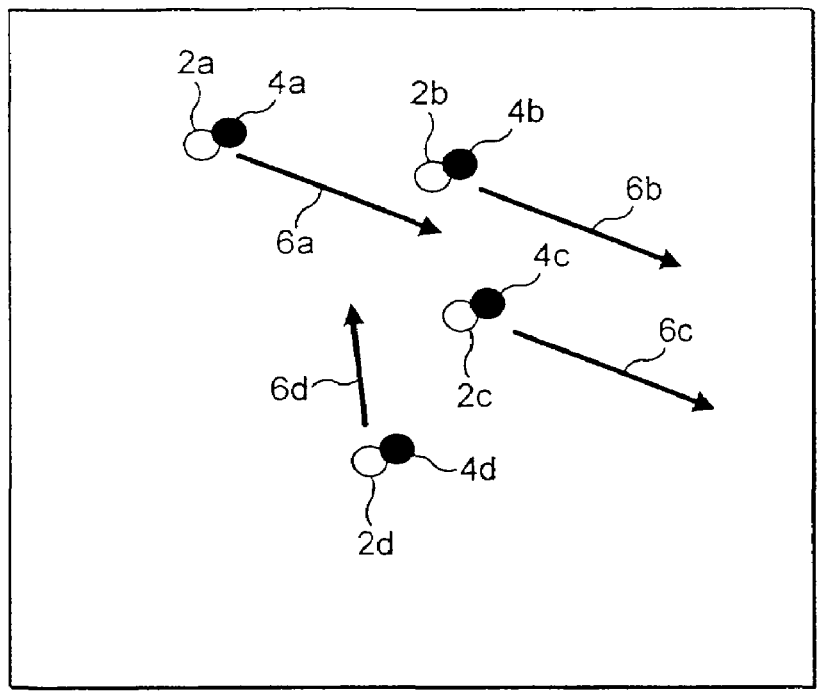
FIGS. 2A and 2B show images of part of a sample at two points in time.
Figure 2B:
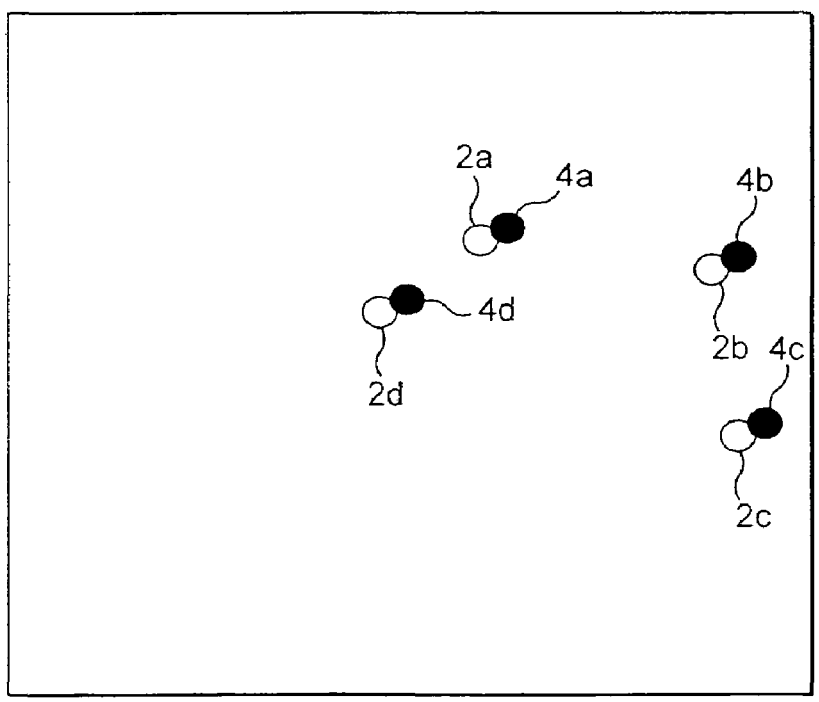
Figure 3B:
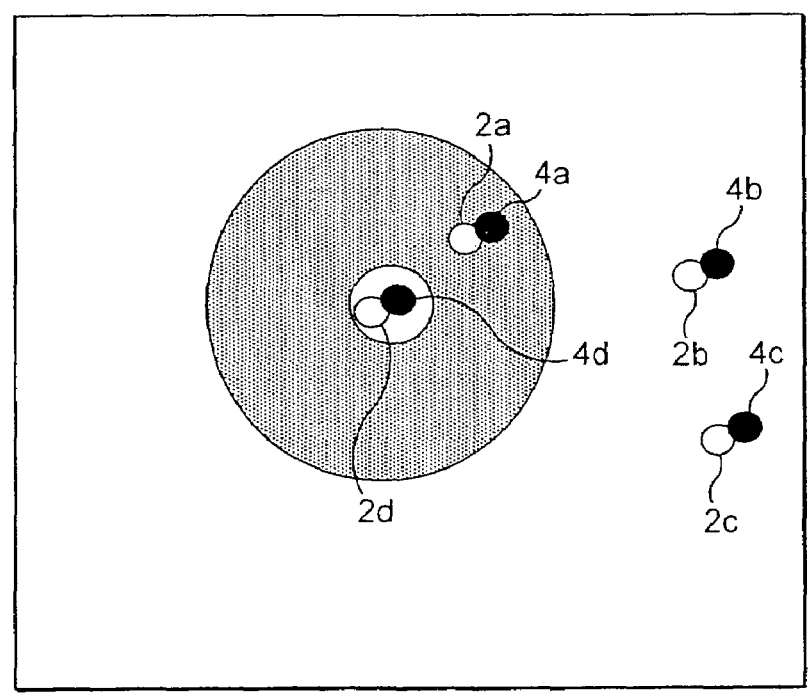

The configurations of particles at two instances of time shown in FIGS. 3A and 3B correspond to those of FIGS. 2A and 2B. However, it can be seen that in FIG. 3B, component 2a and its associated label 4a fall within the region 8 surrounding the component of interest 2d, and its label 4d. Irradiation of region 8 in FIG. 3B bleaches label 4a, making the label 4d optically distinguishable therefrom.

Thus the desired result is achieved by optically modifying (bleaching for example) the neighbouring components but to leave the component of interest unmodified.

The bleached region may be of a doughnut shape, that is, a ring of bleached material. A central, less bleached area of unmodified material, is surrounded by a more bleached region which is optically modified and the region beyond the more bleached area which is also unmodified. The central, less bleached area is preferably somewhat larger than the component of interest, to take into account uncertainty in the position and motion of the component of interest.

The more bleached area is preferably large enough to optically modify all the components likely to be confused with the component of interest, but small enough to permit the instrument to deliver a light dose sufficient to optically modify the neighbouring components without causing damage to the sample (cell).

The more bleached area may for example be scanned in a linear (raster) format, or any vector or dot pattern. Alternatively, the beam itself may be formed into the desired shape, such as an annular shape, for example.

Formation of a laser beam having an annular (or "doughnut") cross-section is described for example in K. S. Youngworth and T. G. Brown, "Focusing of high numerical aperture cylindrical-vector beams," Opt. Express 7, 77-87 (2000); and Gao, C., "New Donut Mode for Optical Tweezers and Spanners," SPIE 4244, pgs 86-89, 2000.

The shape of the irradiated region may be fixed, or may be modified at each time point, based on the information extracted from the image in the view, by instruction from the user, from some other source, or a combination of the three. In this manner neighbouring and potentially interfering components will be bleached and removed from consideration, making continued tracking of the component of interest possible.

Typically, a more bleached area substantially encloses a central, less bleached area, which includes the component of interest. In a preferred embodiment, the central less bleached area is disc-shaped, and the more bleached area is a ring around the less bleached area.

Alternatively, the central less bleached area may be a square, rectangle, arc segment, oblong, or other regular or irregular enclosed shape. Furthermore, the more bleached area may be a square, rectangle, or other regular or irregular enclosed shape, the whole sample or the whole imaging window.

The component of interest may be a cell, part of a cell, or an assembly of cells in one or more fields of view, for example.

More than one less bleached area may be defined, and more than one more bleached region may be formed.

The bleached region may be defined based on the trajectory, route or expected trajectory of the component of interest, thus creating an exclusion zone around the path of the component of interest. In some cases, the region may be based upon the structure of the sample, and may be defined by the shape of the structure, for example, a cell wall, organelle, tubule, and so on.

The time profile of the scanning of the irradiating beam may be non-linear, for example, defining a spiral, with the margin of the irradiated region close to the less bleached area being scanned more slowly and thus receiving an increased light dose. Alternatively a hexagonal scan may be used, which may be easier to implement.

The system may facilitate a simultaneous bleach-and-view process, by the appropriate use of wavelengths and light filtering components. Alternatively, the system may operate by alternating view-then-bleach steps.

The more bleached region may be monitored, and bleaching only applied if any object is observed to be entering the region. This has the advantage of minimizing the amount of light allowed to reach the sample.

The bleaching light and the viewing light may be of different wavelengths and/or different power levels.

Components in a sample may be labeled with one or more fluorescent probes, such as GFP for example, by small molecules such as Fluoroscein, or photoswitching proteins such as KFP1 (described in D. M. Chudakov et al, J. Biol. Chem., 2003, Vol. 278(9), pp. 7215-7219), Kaede (see R. Ando, H. Hama, M. Yamamoto-Hino, H. Mizuno and A. Miyawaki, An optical marker based on the UV-induced green-to-red photoconversion of a fluorescent protein, PNAS, Oct. 1, 2002, vol. 99, no. 20, pp. 12651-12656), and PA-GFP (see J. Lippincott-Schwartz et al, Nature Supp. Imaging in Cell Biol., September 2003, S7-S14).

The sample may be scanned in the Z-direction (that is, perpendicular to the plane of view) to acquire volumetric information. Furthermore, the more bleached region may extend into a different Z-plane than the less bleached region. The more bleached region may be defined above and/or below the component of interest. In particular, this could be used to extend an annular shape to create a weakly enclosed sphere. The region above/below could be formed by modifying the optical path of the bleaching beam and/or using an off-axis path, and/or modulating the beam.

The more bleached region could be part of a sphere. This bleached region could be monitored and bleached according to the actual or predicted trajectory or the component, or other components.

Whilst the description above refers to bleaching of fluorescent labels by irradiation with a light beam, an energy beam (typically a light beam) may also be used to modify the optical properties of labels in other ways to make them distinguishable (photo-switchable labels). For example, the energy beam and labels may be selected such that irradiation causes an increase, rather than a decrease in the intensity of their emissions, in given wavebands (photo-activatable labels).

Irradiation of a sample at different positions along the Z-axis could be carried out using the well-established 2-photon (or multi-photon) mechanism. This requires a high power pulsed laser of longer wavelength (typically 800-1000 nm) which emits very short intense pulses which are focussed at specific Z planes. The fluorescent molecules at this location receive 2 photons almost simultaneously, providing the equivalent energy of 1 photon of half the wavelength, thus bleaching or photomodifying the molecules. Molecules above and below this plane are much less likely to receive two photons so are not affected. This beam may be steered around the particle of interest by moving the sample and/or beam to create the substantially surrounding region.

The invention claimed is:

1. A method of analyzing a sample of biological material including components tagged with respective fluorescent labels, the method comprising the steps of: identifying a specific labeled component to be monitored; and irradiating with an energy beam at least one region of the sample which substantially surrounds said specific component so as to modify the optical properties of labels in the region, such that the label associated with said specific component is distinguishable from those in the region associated with components moving relative to said specific component.

2. A method of claim 1, wherein the at least one region is defined based on the trajectory, path or expected trajectory of the component to be monitored.

3. A method of claim 1, wherein the energy beam may irradiate two or more regions which in combination substantially surround said specific component.

4. A method of claim 1 wherein the at least one region may substantially surround said specific component in two or three dimensions.

5. A method of claim 1 wherein the at least one region defines an enclosed area or volume which is elongate.

6. A method of claim 5 wherein the enclosed area or volume is elongate in the direction of travel of said specific component.

7. A method of claim 1 including one or more farther irradiation steps.

8. A method of claim 1 including the steps of:
monitoring the at least one irradiated region; and
triggering a farther irradiation step in response to detection of additional labeled components entering the at least one region.

9. Apparatus for analyzing a sample of biological material including components tagged with respective fluorescent labels, the apparatus including:
means for irradiating the sample with an energy beam;
a support for holding the sample; and
control means for moving the energy beam and the sample relative to each other to irradiate at least one region of the sample which substantially surrounds the location of a specific component so as to modify the optical properties of labels in the region, such that the label associated with said specific component is distinguishable from those in the region associated with components moving relative to said specific component.

10. Apparatus of claim 9, wherein the at least one region is defined based on the trajectory, path or expected trajectory of the component to be monitored.

* * * * *